US011318115B2

(12) United States Patent
Zhong et al.

(10) Patent No.: US 11,318,115 B2
(45) **Date of Patent: *May 3, 2022**

(54) ORAL PHARMACEUTICAL COMPOSITION OF TECOVIRIMAT AND PREPARATION METHOD THEREOF

(71) Applicant: Institute of Pharmacology and Toxicology Academy of Military Medical Sciences P.L.A. China, Beijing (CN)

(72) Inventors: Wu Zhong, Beijing (CN); Meiyan Yang, Beijing (CN); Wei Gong, Beijing (CN); Yuli Wang, Beijing (CN); Chunsheng Gao, Beijing (CN); Xinbo Zhou, Beijing (CN); Song Li, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 108 days.

This patent is subject to a terminal disclaimer.

(21) Appl. No.: 16/317,942

(22) PCT Filed: Jul. 4, 2017

(86) PCT No.: PCT/CN2017/091648

§ 371 (c)(1),
(2) Date: Jan. 15, 2019

(87) PCT Pub. No.: WO2018/010570

PCT Pub. Date: Jan. 18, 2018

(65) Prior Publication Data

US 2019/0358203 A1 Nov. 28, 2019

(30) Foreign Application Priority Data

Jul. 15, 2016 (CN) ........................ 201610560206.9

(51) Int. Cl.
*A61K 31/4035* (2006.01)
*A61K 47/18* (2017.01)
*A61K 47/40* (2006.01)

(52) U.S. Cl.
CPC .......... *A61K 31/4035* (2013.01); *A61K 47/18* (2013.01); *A61K 47/40* (2013.01)

(58) Field of Classification Search
CPC ..... A61K 47/18; A61K 47/40; A61K 47/6951
See application file for complete search history.

(56) References Cited

U.S. PATENT DOCUMENTS

| | | | |
|---|---|---|---|
| 8,835,501 | B2 | 9/2014 | Bastin et al. |
| 2009/0082400 | A1 | 3/2009 | Lee et al. |
| 2014/0011854 | A1 | 1/2014 | Tyavanagimatt et al. |
| 2019/0336479 | A1 | 11/2019 | Zhong et al. |

FOREIGN PATENT DOCUMENTS

| | | | |
|---|---|---|---|
| AU | 2007246046 | B2 | 11/2007 |
| CN | 1493292 | A | 5/2004 |
| CN | 101062044 | A | 10/2007 |
| CN | 101189003 | A | 5/2008 |
| CN | 102579417 | A | 7/2012 |
| CN | 103281898 | A | 9/2013 |
| CN | 105434345 | A | 3/2016 |
| JP | 2007-529544 | | 10/2007 |
| JP | 2008540499 | A | 11/2008 |
| JP | 2013-532729 | | 8/2013 |
| WO | WO 2005/090380 | A1 | 9/2005 |
| WO | WO 2006-120456 | A1 | 11/2006 |
| WO | WO 2006/120456 | A1 | 11/2006 |
| WO | WO 2009/018326 | A2 | 2/2009 |
| WO | WO 2012/018810 | A9 | 2/2012 |

OTHER PUBLICATIONS

Vakani, S. et al "Influence of auxiliary agents on solubility and dissolution profile . . . " J. Incl. Macrocycl. Chem., vol. 83, pp. 239-250. (Year: 2015).*
Desai, C. et al "Development and evaluation of orally disintegrating tablets . . . " Drug Dev. Ind. Pharm., vol. 41, No. 10, pp. 1589-1607. (Year: 2015).*
Chaudhari, S. et al "Pharmaceutical excipients: a review" Int. J. Adv. Pharm. Biol. Chem., vol. 1, No. 1, pp. 21-34. (Year: 2012).*
Mennini, N. et al "Analysis of physicochemical properties of ternary systems of oxaprozin . . . " J. Pharm. Biomed. Anal., vol. 129, pp. 350-358. (Year: 2016).*
Aloisio, C., et. al., "Solubility and release modulation effect of sulfamerazine ternary complexes with cyclodextrins and meglumine." Journal of Pharmaceutical and Biomedical Analysis, 100:64-73 (2014).
Office action and search report for Chinese Patent Application No. 201610560206.9, dated May 28, 2020, China National Intellectual Property Administration, Beijing City, China.
Office action and search report for Chinese Patent Application No. 201610560206.9, dated May 7, 2019, China National Intellectual Property Administration, Beijing City, China.
Feng-ying, et. al., "Determination of the equilibrium solubility of tecovirimat and its apparent oil/water partition coefficients using HPLC." Mil. Med. Sci., 36(1):49-51, 55 (Jan. 2012).

(Continued)

*Primary Examiner* — Leigh C Maier

(74) *Attorney, Agent, or Firm* — Sterne, Kessler, Goldstein & Fox P.L.L.C.

(57) ABSTRACT

The present invention relates to a pharmaceutical composition, comprising Tecovirimat, cyclodextrin and an additive, and optionally a pharmaceutically acceptable excipient. The present invention also relates to a method for preparing the pharmaceutical composition. The composition improves the solubility of Tecovirimat in water by using cyclodextrin and meglumine in combination, as compared with the solubility of Tecovirimat in water by using cyclodextrin or meglumine alone.

16 Claims, 3 Drawing Sheets

(56) References Cited

OTHER PUBLICATIONS

Lee, J.W., et. al., "Preparation and Evaluation of Inclusion Complex of Lansoprazole with 2-HP-β-Cyclodextrin and Meglumine." J. Kor. Pharm. Sci, 34(4):269-274 (2004).
International Search Report (ISR) for PCT/CN2017/091648; I.A. fd: Jul. 4, 2017; dated Oct. 11, 2017, State Intellectual Property Office of the P.R. China, Beijing, China.
International Preliminary Report on Patentability (IPRP) (Chapter II of the Patent Cooperation Treaty; PCT Article 36 and Rule 70) for PCT/CN2017/091648; I.A. fd: Jul. 4, 2017; dated Nov. 10, 2018, by The International Bureau of WIPO, Geneva, Switzerland.
Sangwai, M., et. al., "Amorphous ternary cyclodextrin nanocomposites of telmisartan for oral drug delivery: Improved solubility and reduced pharmacokinetic variability." Int. J. of Pharmaceutics, 453:423-432 (2013).
Basavaraj, S., et. al., "Bioavailability Enhancement of Poorly Water Soluble and Weakly Acidic New Chemical Entity with 2-Hydroxy Propyl-β-Cyclodextrin: Selection of Meglumine, a Polyhydroxy Base, as a Novel Ternary Component." Pharma. Dev. and Tech. 11:443-451 (2006).
Office action for Japanese Patent Application No. 2019-501450, dated Jul. 29, 2019, The Japan Patent Office, Tokyo, Japan.
Restriction requirement dated Nov. 2, 2020, and Reply to Restriction requirement filed Dec. 18, 2020, in U.S. Appl. No. 16/318,044, Zhong et al. 371 date; Jan. 15, 2019.
Office action dated Jan. 26, 2021, in U.S. Appl. No. 16/318,044, Zhong et al. 371 date; Jan. 15, 2019.

* cited by examiner

ORAL PHARMACEUTICAL COMPOSITION OF TECOVIRIMAT AND PREPARATION METHOD THEREOF

TECHNICAL FI a preferred filler is selected from the group consisting of lactose, complex lactose, microcrystalline cellulose, anhydrous calcium dihydrogen phosphate, mannitol, starch, and pregelatinized starch;

a preferred binder is selected from the group consisting of polyvinyl pyrrolidone, hydroxypropyl methylcellulose, and hydroxymethyl cellulose;

a preferred disintegrating agent is selected from the group consisting of cross-linked polyvinyl pyrrolidone, carboxymethyl starch sodium, croscarmellose sodium, and low-substituted hydroxypropyl cellulose;

a preferred lubricant is selected from the group consisting of talc powder, magnesium stearate, hydrogenated castor oil, and Aerosil.

8. The pharmaceutical composition according to any one of Items 1 to 7 of the present invention, comprising Tecovirimat, cyclodextrin (e.g. 2-hydroxypropyl-β-cyclodextrin), an additive (e.g. meglumine), lactose, hydroxypropyl methylcellulose, carboxymethyl starch sodium, and Aerosil, at a weight ratio of 40~100:80~120:200~400:20~50:1~4:8~12:1~4, preferably 50:100:300:35.5:2:10.0:2.5 or 70:100:300:15.5:2:10.0:2.5.

9. A method for preparing the pharmaceutical composition according to any one of Items 1 to 8 of the present invention, comprising:

a) dissolving an additive and cyclodextrin in a desired volume of water, and mixing well;

b) adding Tecovirimat, and mixing well;

c) removing water by drying, wherein a preferred drying is freeze-drying or spray-drying;

d) adding a filler, a binder, and a disintegrating agent, sieving with an 80-mesh sieve, and mixing well;

e) compressing directly, or adding a non-aqueous solvent (e.g. ethanol) as a wetting agent to prepare a soft material, preparing wet granules, drying the wet granules to obtain dry granules, adding a lubricant to the dry granules, mixing, breaking, and preparing tablets, or adding a lubricant, and preparing capsules or granules.

10. A method for treating smallpox, comprising administering to a subject in need thereof a therapeutically and/or prophylactically effective amount of the pharmaceutical composition according to any one of Items 1 to 8 of the present invention.

11. The pharmaceutical composition according to any one of Items 1 to 8 of the present invention, for use in the treatment of smallpox.

12. Use of the pharmaceutical composition according to any one of Items 1 to 8 of the present invention for the manufacture of a medicament for treating smallpox.

In a particular embodiment, the pharmaceutical composition according to the present invention is an oral preparation, such as a granule (e.g. an instant granule), a capsule, or a tablet.

When the pharmaceutical composition according to the present invention is an oral preparation, it can be prepared by the following method comprising:

a. dissolving an additive and cyclodextrin in a desired volume of water, and mixing well;

b. adding the active ingredient-Tecovirimat, and stirring in a water bath;

c. removing water from the prepared solution by spray-drying;

d. adding a filler, a binder, and a disintegrating agent, mixing, sieving with an 80-mesh sieve, and mixing well;

e. adding a wetting agent (e.g. 50% (w/w) ethanol);

f. preparing a soft material with the as-prepared mixture, sieving with a 20-mesh sieve to prepare wet granules, and drying the wet granules at 60° C. to obtain dry granules;

g. adding a given amount of a lubricant to the dry granules, sieving with a 16-mesh sieve, mixing, breaking, and preparing tablets.

When the pharmaceutical composition according to the present invention is an oral preparation, it can also be prepared by another method comprising:

a. dissolving an additive and cyclodextrin in a desired volume of water, and mixing well;

b. adding the active ingredient-Tecovirimat, an stirring in a water bath;

c. removing water from the prepared solution by freeze-drying;

d. adding a filler, a binder, and a disintegrating agent, mixing, sieving with an 80-mesh sieve, and mixing well;

e. adding a wetting agent (e.g. 50% (w/w) ethanol);

f. using said mixing material to prepare a soft material, sieving with a 20-mesh sieve to prepare wet granules, and drying the wet granules at 60° C. to obtain dry granules;

g. adding a given amount of a lubricant to the dry granules, sieving with a 16-mesh sieve, mixing, breaking, and preparing tablets.

When the pharmaceutical composition according to the present invention is an oral preparation, it can also be prepared by another method comprising:

a. dissolving an additive and cyclodextrin in a desired volume of water, and mixing well;

b. adding the active ingredient-Tecovirimat, and stirring in a water bath;

c. removing water from the prepared solution by freeze-drying;

d. adding a filler, a binder, a disintegrating agent, and a lubricant, mixing, sieving with an 80-mesh sieve, and mixing well;

e. compressing directly to prepare tablets.

When the pharmaceutical composition according to the present invention is an oral preparation, it can also be prepared by another method comprising:

a. dissolving an additive and cyclodextrin in a desired volume of water, and mixing well;

b. adding the active ingredient-Tecovirimat, under stirring in a water bath;

c. removing water from the prepared solution by freeze-drying;

d. adding a filler, a binder, a disintegrating agent, and a lubricant, mixing, sieving with an 80-mesh sieve, and mixing well;

e. filling directly to prepare capsules.

When the pharmaceutical composition according to the present invention is an oral preparation, it can also be prepared by another method comprising:

a. dissolving an additive and cyclodextrin in a desired volume of water, and mixing well;

b. adding the active ingredient-Tecovirimat, and stirring in a water bath;

c. removing water from the prepared solution by freeze-drying;

d. adding a filler, a binder, a disintegrating agent, and a lubricant, mixing, sieving with an 80-mesh sieve, and mixing well;

e. filling directly to prepare instant granules.

In the present invention, the term "an additive" refers to a substance that can interact with an active ingredient, so as to enhance the inclusion efficiency of cyclodextrin, and further to improve drug solubility.

In the present invention, the term "soft material" refers to a wet mixture formed in a wet granulation process in which a suitable amount of a wetting agent or a binder are added to raw material and subsidiary material to form a mixture and the mixture is wetted to form a wet mixture.

In the present invention, "% (w/v)" refers to a mass/volume concentration, which represents the mass (expressed as gram) of a solute contained in a solution (100 ml). For example, 20% (w/v) represents 20 g of a solute contained in a solution (100 ml).

DESCRIPTION OF THE DRAWINGS

FIG. 1 shows the solubility curves of Tecovirimat in different solutions at 25° C., 37° C. and 60° C., wherein:

SPECIFIC MODES FOR CARRYING OUT THE INVENTION

Figure 1A:
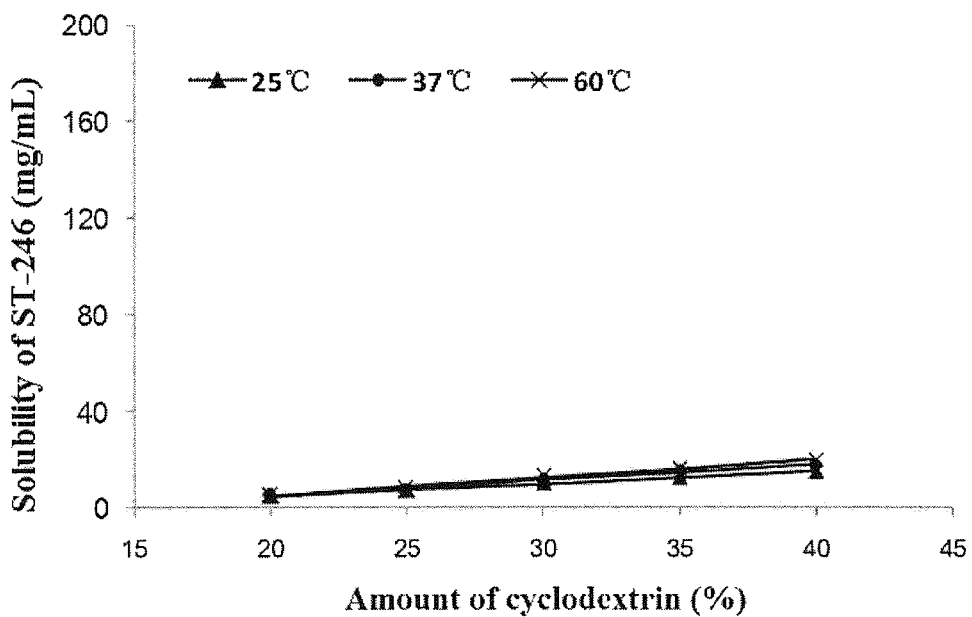
FIG. 1(A) shows the solubility curve of Tecovirimat in a solution containing 2-hydroxypropyl-β-cyclodextrin alone.

The embodiments of the present invention are described in detail by combining the following examples. However, a person skilled in the art will understand that the following examples and experimental examples are only used to describe the present invention, and should not be regarded as defining the scope of the present invention. In the case where the concrete conditions are not indicated in the examples and experimental examples, the examples are carried out according to conventional conditions or the conditions recommended by manufacturers. The reagents or apparatuses, the manufacturers of which are not indicated, are the conventional products that are commercially available.

Example 1: Preparation of an Oral Solubilizing Composition Containing Tecovirimat

TABLE 1

| | Formulation | | |
|---|---|---|---|
| | Amount of raw materials (g/1000 formulation unit*) | | |
| Name of raw materials | Ternary composition (Tecovirimat/ meglumine/ cyclodextrin) | Binary composition (Tecovirimat/ meglumine) | Binary composition (Tecovirimat/ cyclodextrin) |
| Tecovirimat | 100.0 | 100.0 | 100.0 |
| meglumine | 200.0 | 200.0 | / |
| hydroxypropyl-β-cyclodextrin | 600.0 | / | 600.0 |
| lactose | 71 | 671 | 271 |
| hydroxypropyl methylcellulose | 4 | 4 | 4 |
| carboxymethyl starch sodium | 20 | 20 | 20 |
| Aerosil | 5 | 5 | 5 |

*as calculated on the basis of a daily dose of 200 mg for Tecovirimat, the solid preparation is designed to comprise 100 mg Tecovirimat per preparation unit, i.e. twice a day, 1 preparation unit for each time.

In order to compare the dissolution characteristics of the drug, binary compositions (Tecovirimat/meglumine, Tecovirimat/cyclodextrin), and a ternary composition (Tecovirimat/meglumine/cyclodextrin), based on the Formulation in Table 1, tablets of a ternary composition (Tecovirimat/meglumine/cyclodextrin), a binary composition (Tecovirimat/meglumine), and a binary composition (Tecovirimat/cyclodextrin) were prepared, in which lactose was used to adjust the weight.

Preparation method: based on the prescribed amounts in the Formulation as described in Table 1, meglumine and hydroxypropyl-β-cyclodextrin were weighed, dissolved in a desired volume of water, and mixed well; a prescribed amount of the active ingredient-Tecovirimat was further added, under stirring in a water bath; water was removed from the prepared solution by freeze-drying; lactose (a filler), hydroxypropyl methylcellulose (a binder), and carboxymethyl starch sodium (a disintegrating agent) were added and mixed, then the resultant was sieved with an 80-mesh sieve, and mixed well; 50% (w/w) ethanol as a wetting agent was further added; the mixed material was prepared into a soft material, the soft material was sieved with a 20-mesh sieve to prepare wet granules, and the wet granules were dried at 60'C to obtain dry granules; to the dry granules, a prescribed amount of Aerosil (a lubricant) was added, and the resultant was sieved with 16-mesh sieve, broke, and compressed into tablets, or the resultant was subjected to filling directly to prepare instant granules.

Experimental Example 1: Solubility Test

Excess amounts of Tecovirimat (bulk drug powder) was added to an aqueous solution comprising meglumine and cyclodextrin at different ratios relative to each other to form a suspension. The suspension was placed in a constant-temperature incubation shaker, and was shaken at a temperature of 25±1° C., 37±1° C. and 60±1° C. for 72 h. After reaching equilibrium, the suspension was filtered through a 0.45 μm hydrophilic filter membrane to obtain a filtrate. After the filtrate was properly diluted with an acetonitrile-water (50:50, v/v) solution, the absorbance was measured at 224 nm, and the solubility of Tecovirimat was calculated. The corresponding solubility curve was plotted by using the solubility of the drug as the ordinate, and using the concentration of the cyclodextrin and/or meglumine as the abscissa. The solubility curves of Tecovirimat at 25° C., 37° C. and 60° C. were shown in FIG. 1(A) to FIG. 1(C).

As seen from FIG. 1(A), the solubility of Tecovirimat in water increased linearly with the increase in the amount of cyclodextrin: when the amount of cyclodextrin was in the range from 20% (w/v) to 40% (w/v), the solubility of Tecovirimat in water at 25° C., 37° C. and 60° C. was from 5 mg/ml to 15 mg/ml, from 5 mg/ml to 18 mg/ml, and from 5 mg/ml to 20 mg/ml, respectively.

Figure 1B:
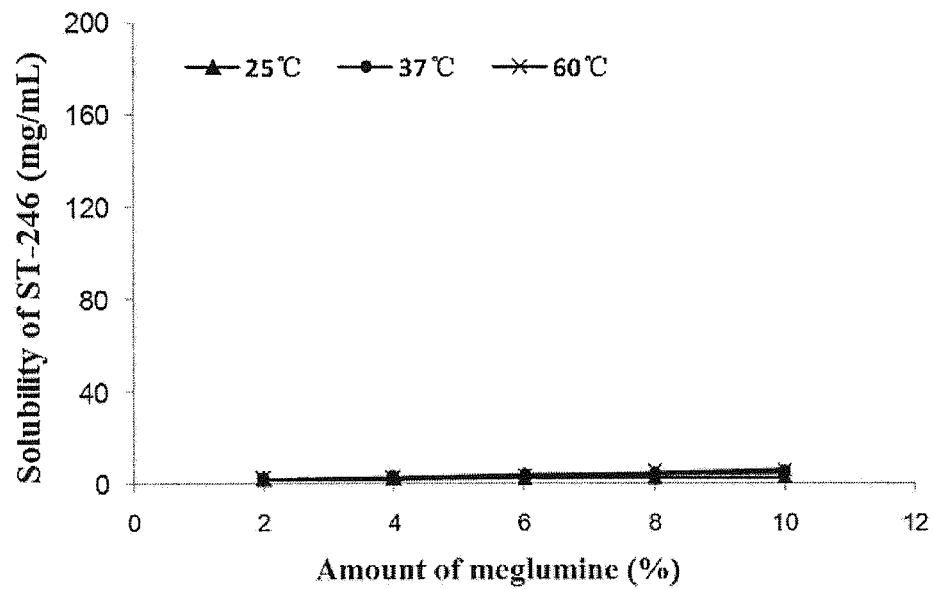
FIG. 1(B) shows the solubility curve of Tecovirimat in a solution containing meglumine alone.

As seen from FIG. 1(B): the solubility of Tecovirimat in water also increased linearly with the increase in the amount of meglumine: when the amount of meglumine was in a range from 2% (w/v) to 10% (w/v), the solubility of Tecovirimat in water at 25° C., 37° C. and 60° C. was from 2 mg/ml to 7 mg/ml, from 2 mg/ml to 9 mg/ml, and from 2 mg/ml to 10 mg/ml, respectively.

Figure 1C:
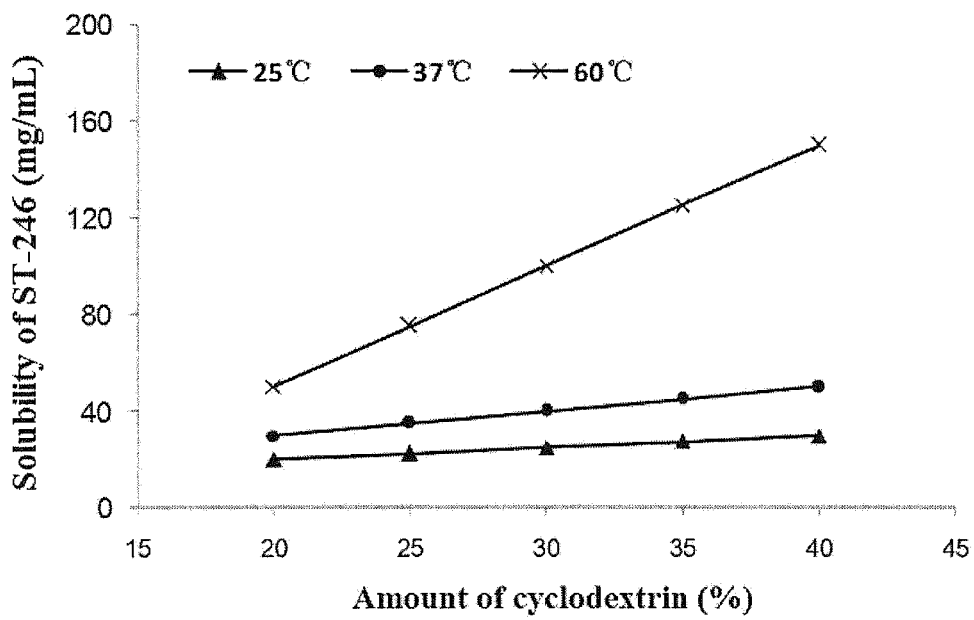
FIG. 1(C) shows the solubility curve of Tecovirimat in a solution containing both 2-hydroxypropyl-β-cyclodextrin and meglumine (the amount of meglumine is 5%).

As seen from FIG. 1(C): the use of cyclodextrin and meglumine in combination could significantly increase the solubility of Tecovirimat in water. When the amount of meglumine was 5% (w/v) and the amount of cyclodextrin was in a range from 20% (w/v) to 40% (w/v), the solubility of Tecovirimat in water at 25° C., 37° C. and 60° C. was from 20 mg/ml to 80 mg/ml, from 30 mg/ml to 100 mg/ml, and from 50 mg/ml to 150 mg/ml, respectively. This indicated that meglumine and cyclodextrin had an unexpected synergistic effect on the solubility of Tecovirimat.

According to the results of the phase solubility test, when the amount of cyclodextrin was in a range from 5% to 40%, the thermodynamic parameters were calculated for the formation of a drug-cyclodextrin inclusion complex. The result was shown in Table 5. A negative $\Delta G$ indicated that the inclusion process could occur spontaneously; a positive $\Delta H$ indicated that the main driving force of inclusion process was hydrophobic interaction, and meanwhile the inclusion process was an endothermic reaction, so the inclusion reaction could be promoted by increasing the temperature properly. However, the ternary composition has a lower value of $\Delta H$, because the entrance of meglumine into the cavity resulted in release of more enthalpy-rich water; a positive $\Delta S$ indicated that the inclusion process was an enthalpy increasing process, and the ternary composition has a lower value of $\Delta S$, because the degree of freedom for Tecovirimat and meglumine in the cavity was reduced, thereby a more stable inclusion system was formed.

was filtrated through a 0.45 μm microporous membrane, to obtain a test solution; and Tecovirimat (bulk drug powder, 5 mg) as a reference was accurately weighed, and placed in a 100 ml volumetric flask, and the medium for dissolution was added to a final volume of 100 ml, thereby obtaining a reference solution. By high performance liquid chromatography, the peak area of the test solution and the reference solution were measured at 224 nm. The dissolution amounts at different time points was calculated by an external standard method, and the cumulative dissolution curves were plotted.

Figure 2:
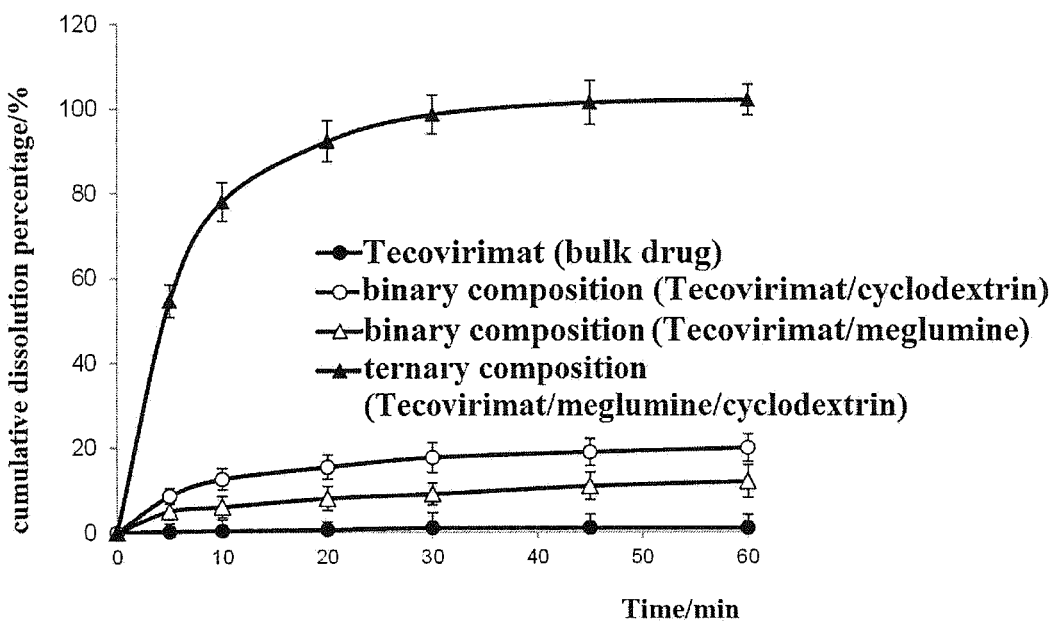
FIG. 2 shows the dissolution curves of the tablet of the oral solubilizing pharmaceutical composition of Tecovirimat prepared in Example 1 and Tecovirimat (bulk drug) in water.

The dissolution curves were shown in FIG. 2. The result shows that the oral tablets of the ternary solubilizing composition (Tecovirimat/meglumine/cyclodextrin) as prepared in Example 1 had a complete dissolution of 100% within 30 min, while the tablet of the binary composition (Tecovirimat/cyclodextrin), the tablet of the binary composition (Tecovirimat/meglumine), and Tecovirimat (bulk drug) had a dissolution of less than 20%, 15%, and 5% within 60 min, respectively.

Experimental Example 3: Nuclear Magnetic Resonance (NMR) Spectroscopic Assay

Experimental method: a suitable amount of Tecovirimat, meglumine, cyclodextrin, a binary composition of Tecovirimat and meglumine (Tecovirimat/meglumine at a weight ratio of 1:2), a binary composition of Tecovirimat and cyclodextrin (Tecovirimat/cyclodextrin at a weight ratio of 1:6), and a ternary composition of Tecovirimat, meglumine and cyclodextrin (Tecovirimat/meglumine/cyclodextrin at a weight ratio of 1:2:6) were dissolved in DMSO-d6 to prepare samples, respectively, and the possible intermolecular interaction was analyzed by $^1$H NMR spectroscopy.

Figure 3:
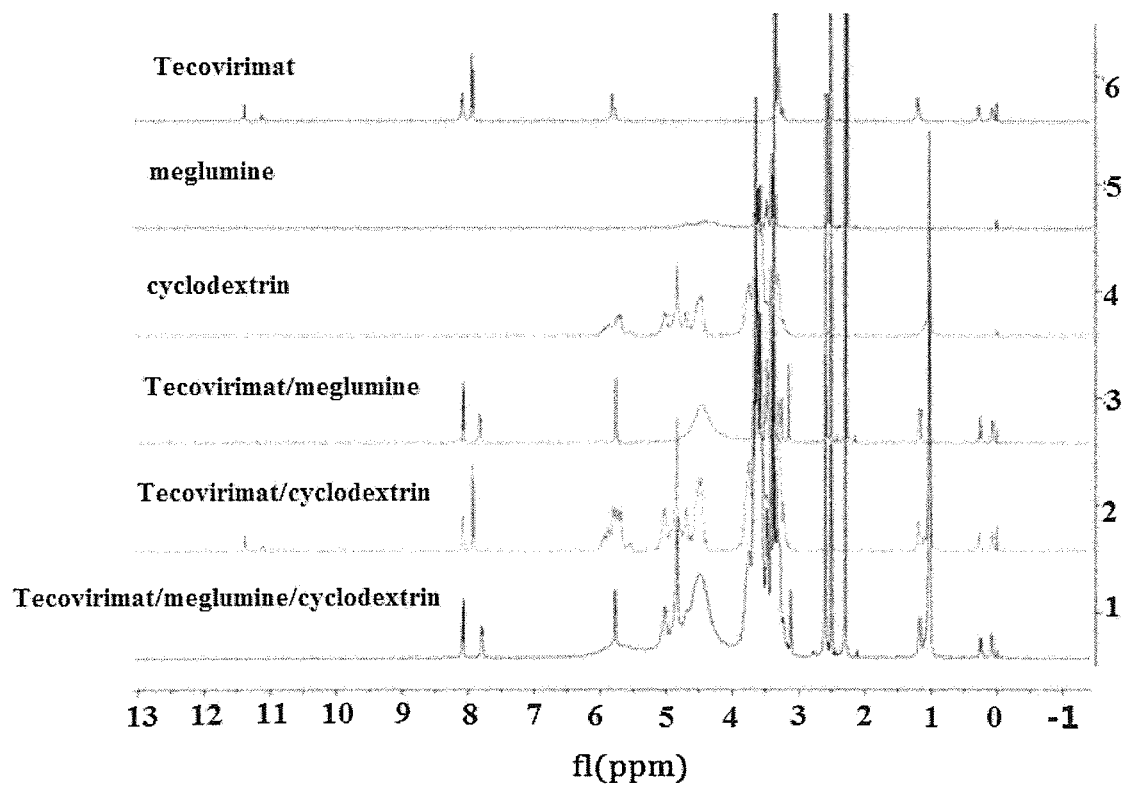
FIG. 3 shows $^1$H Nuclear Magnetic Resonance (NMR) spectra of Tecovirimat, meglumine, cyclodextrin, binary compositions (Tecovirimat/meglumine, Tecovirimat/cyclodextrin), and a ternary composition (Tecovirimat/meglumine/cyclodextrin).

Experimental result: the NMR spectra were shown in FIG. 3, and it was deduced by chemical shift results that hydrogen bonds were formed between Tecovirimat and meglumine, while the presence of meglumine changed the steric structure of Tecovirimat; when Tecovirimat entered the cavity of cyclodextrin, electrostatic interaction occurred

TABLE 5

Thermodynamic parameters of different solubilizing compositions

| Components of a solution | Drug concentration (mg/ml) | MEG Amount % (w/v) | $\Delta G$ (KJ/mol) 25° C. | $\Delta G$ (KJ/mol) 37° C. | $\Delta G$ (KJ/mol) 60° C. | $\Delta H$ (KJ/mol) | $\Delta S$ (J/mol K) |
|---|---|---|---|---|---|---|---|
| Tecovirimat/cyclodextrin | 5~20 | 0 | −8.782 | −9.610 | −11.197 | 11.780 | 0.069 |
| Tecovirimat/cyclodextrin/0.25% meglumine | 6~24 | 0.25% (w/v) | −6.712 | −7.420 | −8.777 | 10.870 | 0.059 |
| Tecovirimat/cyclodextrin/1% meglumine | 7~26 | 1.0% (w/v) | −4.614 | −5.190 | −6.294 | 9.690 | 0.048 |

Note:
among the components of the solution, the amount of cyclodextrin was 5%~40% (w/v)

Experimental Example 2: In Vitro Dissolution

Experimental method: 1000 ml water was used as dissolution medium, and according to the Dissolution Test (Pharmacopoeia of the People's Republic of China (2015 Edition), General Notices, 0931 Method II), the operation was carried out at a rotation rate of 100 rpm, and a solution (5 ml) was taken at 5, 10, 15, 30, 45, and 60 min, respectively, and between Tecovirimat and cyclodextrin. Therefore, the solubilization of Tecovirimat was resulted from the interactions of the components in the ternary composition, which were mainly hydrogen bonding interaction and inclusion interaction.

To sum up, as compared with the prior art, the present invention provides an oral pharmaceutical composition of Tecovirimat, in which the inclusion efficiency of cyclodextrin is enhanced greatly because the addition of an additive makes the drug to be included more easily. The synergistic action of them greatly improves the in vitro dissolution of the poorly soluble drug Tecovirimat, and meanwhile, reduces the amount of cyclodextrin used, and therefore reduces the potential medicament risk. The oral pharmaceutical composition also has the advantages such as simple formulation, low cost, easy operation, stable and controllable quality, and good reproducibility.

That invention claimed is:

1. A pharmaceutical composition, comprising Tecovirimat, cyclodextrin and an additive, and optionally a pharmaceutically acceptable excipient, wherein said additive is meglumine; wherein said cyclodextrin is selected from the group consisting of dimethyl-β-cyclodextrin, 2-hydroxyethyl-β-cyclodextrin, 2-hydroxypropyl-β-cyclodextrin, 3-hydroxypropyl-β-cyclodextrin, and trimethyl-β-cyclodextrin.

2. The pharmaceutical composition according to claim 1, wherein said cyclodextrin and Tecovirimat have a weight ratio of 4~10:1.

3. The pharmaceutical composition according to claim 1, wherein said additive and Tecovirimat have a weight ratio of 0.5~5:1.

4. The pharmaceutical composition according to claim 1, wherein said additive and cyclodextrin have a weight ratio of 1:1~5.

5. The pharmaceutical composition according claim 1, wherein said pharmaceutical composition is an oral preparation, an injection, an infusion solution, drops, a patch, a liniment, an enema or an implant.

6. The pharmaceutical composition according to claim 1, wherein said pharmaceutically acceptable excipient is selected from the group consisting of a filler, a binder, a disintegrating agent, a lubricant, a correctant, a coloring agent, a taste masking agent, a pH adjuster, a buffering agent, a preservative, a stabilizer, an antioxidant, a wetting agent, a humidity adjusting agent, a surfactant, a suspending agent and an absorption enhancer.

7. The pharmaceutical composition according to claim 1, comprising Tecovirimat, cyclodextrin, an additive, lactose, hydroxypropyl methylcellulose, carboxymethyl starch sodium, and fumed silica lubricant, at a weight ratio of 40~100:80~120:200~400:20~50:1~4:8~12:1~4.

8. A method for preparing the pharmaceutical composition according to claim 1, comprising:
    a) dissolving the additive and cyclodextrin in a desired volume of water, and mixing well;
    b) adding Tecovirimat, and mixing well;
    c) removing water by drying;
    d) adding a filler, a binder, and a disintegrating agent, sieving with an 80-mesh sieve, and mixing well;
    e) compressing directly, or adding a non-aqueous solvent as a wetting agent to prepare a soft material, preparing wet granules, drying the wet granules to obtain dry granules, adding a lubricant to the dry granules, mixing, breaking, and preparing tablets, or
    adding a lubricant, and preparing capsules or granules.

9. A method for treating smallpox, comprising administering to a subject in need thereof a therapeutically and/or prophylactically effective amount of the pharmaceutical composition according to claim 1.

10. The pharmaceutical composition according to claim 1, wherein said cyclodextrin is selected from the group consisting of 2-hydroxypropyl-β-cyclodextrin, and 3-hydroxypropyl-β-cyclodextrin.

11. The pharmaceutical composition according to claim 1, wherein said cyclodextrin is 2-hydroxypropyl-β-cyclodextrin.

12. The pharmaceutical composition according to claim 1, wherein at least one of the following is satisfied:
    said cyclodextrin and Tecovirimat have a weight ratio of 5~8:1;
    said additive and Tecovirimat have a weight ratio of 1~4:1;
    said additive and cyclodextrin have a weight ratio of 1:2~4.

13. The pharmaceutical composition according to claim 1, wherein at least one of the following is satisfied:
    said cyclodextrin and Tecovirimat have a weight ratio of 5:1, 6:1, 7:1 or 8:1;
    said additive and Tecovirimat have a weight ratio of 1:1, 2:1, 3:1, or 4:1;
    said additive and cyclodextrin have a weight ratio of 1:3.

14. The pharmaceutical composition according to claim 1, wherein said pharmaceutical composition is an oral preparation, an injection or an infusion solution.

15. The pharmaceutical composition according to claim 6, wherein at least one of the following is satisfied:
    said pharmaceutically acceptable excipient is selected from the group consisting of a filler, a binder, a disintegrating agent, and a lubricant;
    the filler is selected from the group consisting of lactose, complex lactose, microcrystalline cellulose, anhydrous calcium dihydrogen phosphate, mannitol, starch, and pregelatinized starch;
    the binder is selected from the group consisting of polyvinyl pyrrolidone, hydroxypropyl methylcellulose, and hydroxymethyl cellulose;
    the disintegrating agent is selected from the group consisting of cross-linked polyvinyl pyrrolidone, carboxymethyl starch sodium, croscarmellose sodium, and low-substituted hydroxypropyl cellulose;
    the lubricant is selected from the group consisting of talc powder, magnesium stearate, hydrogenated castor oil, and fumed silica lubricant.

16. The pharmaceutical composition according to claim 7, wherein at least one of the following is satisfied:
    said cyclodextrin is 2-hydroxypropyl-β-cyclodextrin;
    said pharmaceutical composition comprises Tecovirimat, cyclodextrin, an additive, lactose, hydroxypropyl methylcellulose, carboxymethyl starch sodium, and fumed silica lubricant, at a weight ratio of 50:100:300:35.5:2:10.0:2.5 or 70:100:300:15.5:2:10.0:2.5.

* * * * *